United States Patent
Powers et al.

(10) Patent No.: US 7,469,416 B2
(45) Date of Patent: Dec. 23, 2008

(54) METHOD FOR AUTOMATICALLY MANAGING INFORMATION PRIVACY

(75) Inventors: Calvin S. Powers, Chapel Hill, NC (US); Martin Presler-Marshall, Chapel Hill, NC (US)

(73) Assignee: International Business Machines Corporation, Armonk, NY (US)

( * ) Notice: Subject to any disclaimer, the term of this patent is extended or adjusted under 35 U.S.C. 154(b) by 700 days.

(21) Appl. No.: 10/288,082

(22) Filed: Nov. 5, 2002

(65) Prior Publication Data

US 2004/0088579 A1 May 6, 2004

(51) Int. Cl.
*G06F 21/00* (2006.01)
(52) U.S. Cl. .................. 726/1; 726/4; 726/27; 726/28; 726/29; 726/30; 707/2; 707/3; 707/9; 705/3; 705/51
(58) Field of Classification Search ............. 726/27–30, 726/1, 4; 707/2, 3, 9, 103 R; 705/3, 51, 705/26, 27
See application file for complete search history.

(56) References Cited

U.S. PATENT DOCUMENTS

| | | | |
|---|---|---|---|
| 5,922,074 A | 7/1999 | Richard et al. | |
| 5,940,507 A | 8/1999 | Cane et al. | |
| 5,987,608 A | 11/1999 | Roskind | |
| 6,158,007 A | 12/2000 | Moreh et al. | |
| 6,249,873 B1 | 6/2001 | Richard et al. | |
| 6,256,393 B1 | 7/2001 | Safadi et al. | |
| 6,275,824 B1 | 8/2001 | O'Flaherty et al. | |
| 6,278,999 B1 | 8/2001 | Knapp | |
| 6,327,535 B1 | 12/2001 | Evans et al. | |
| 6,360,102 B1 | 3/2002 | Havinis et al. | |
| 6,845,448 B1 * | 1/2005 | Chaganti et al. | 713/166 |
| 6,947,897 B2 * | 9/2005 | Lortscher et al. | 705/14 |
| 6,954,757 B2 * | 10/2005 | Zargham et al. | 707/101 |
| 2003/0004734 A1 * | 1/2003 | Adler et al. | 705/1 |
| 2003/0074564 A1 * | 4/2003 | Peterson | 713/182 |
| 2003/0208454 A1 * | 11/2003 | Rienhoff et al. | 707/1 |
| 2003/0229529 A1 * | 12/2003 | Mui et al. | 705/8 |
| 2005/0086061 A1 * | 4/2005 | Holtmanns et al. | 705/1 |
| 2005/0102194 A1 * | 5/2005 | Kuehr-McLaren et al. | 705/26 |

FOREIGN PATENT DOCUMENTS

| | | |
|---|---|---|
| EP | 1132796 A1 | 9/2001 |
| WO | WO 00/50978 | 8/2000 |

(Continued)

OTHER PUBLICATIONS http://www.java.sun.com/j2ee/tutorial/1_3-fcs/index.html, "The J2EE Tutorial", Apr. 24, 2002.*

(Continued)

*Primary Examiner*—Kambiz Zand
*Assistant Examiner*—Tongoc Tran
(74) *Attorney, Agent, or Firm*—A. Bruce Clay; Hoffman Warnick LLC

(57) ABSTRACT

A request including a call for the information in a bean and a purpose for the call is received. Upon receipt, the purpose is compared to a privacy control policy that is packaged with the bean. If the purpose complies with the privacy control policy, the requested access and/or use of the information is permitted.

15 Claims, 2 Drawing Sheets

FOREIGN PATENT DOCUMENTS

| | | |
|---|---|---|
| WO | WO 0052900 A1 | 9/2000 |
| WO | WO 0150400 A1 | 7/2001 |

OTHER PUBLICATIONS http://www.oracle.com, "Enterprise JavaBeans Samples", 2004.*

Monson-Haefel, "Enterprise JavaBeans", 2000, O'Reilly, 2nd edition, pp. 1-2, 30-35 and 3948.*

Research Disclosure, Oct. 2000, 438067, "Privacy Informant—CYM Standards", author Unknown: 438068, "An Extension of an Operating System Interface that Re-enables Peripheral Tasks", Author Unknown.

Research Disclosure, Mar. 2000, p. 583, 431170, "Reconfigurable User Interfaces at Various Levels of Complexity", IBM, 431171, "Restriction Strategies on Extraneous Domain Inline Embedded Objects in HTML", IBM.

Nikander et al, "Distributed Policy Management for JDK 1.2", Date Unknown.

* cited by examiner

METHOD FOR AUTOMATICALLY MANAGING INFORMATION PRIVACY

BACKGROUND OF THE INVENTION

1. Field of the Invention

In general, the present invention relates to a method, system and program product for automatically managing information privacy. Specifically, the present invention allows a request for information to be examined against a privacy control policy to ensure compliance with privacy control rules.

2. Background Art

As the use of the world wide web grows, computer users are increasingly conducting everyday transactions on-line. For example, today a user can purchase clothing, order prescriptions, pay bills, etc. In conducting such transactions, however, the users are typically required to provide personal information. Such information can include items such as name, address, credit card number, electronic mailing (e-mail) address, etc. Once provided, it is common for this information to be stored in a JavaBean or Enterprise JavaBean (EJB). As known in the art, a bean is a program component that generally includes data (i.e., the information) and methods (i.e., procedures that operate on the data). Storing information in a bean generally makes it easier to later access or utilize the information .

Unfortunately, when personal information is provided and stored in this manner, privacy becomes a major concern. Currently, many companies who conduct business online have internal privacy control policies that dictate what the company will (and will not) do with the information submitted by a user. These policies often work in conjunction with the wishes of the users. For example, when placing an order with a particular company, the interface operated by the user could include a "check box" for the user to indicate whether he/she wishes to receive future e-mail messages from the company. Thus, a rule in the company's privacy control policy could dictate that a user's e-mail address can only be used if the appropriate "check box" had been selected. If an employee of the company attempted to send an e-mail message to a user who had not checked the box, the rule would be broken.

Heretofore, attempts to protect information privacy have been tedious and time consuming. Specifically, a programmer writing an application that is used to access information had to manually code the privacy considerations into the application. This is especially tedious when a company has multiple applications that can access the information. Moreover, each time a privacy control policy changes, the application that it is coded into will have to be updated. Accordingly, no existing system is provided for automating the implementation and enforcement of privacy control policies. That is, no system currently provides automatic management of information privacy.

In view of the foregoing, there exists a need for a method, system and program product for automatically managing information privacy. Specifically, a need exists for a user's submitted information to be stored in a bean and packaged with a privacy control policy. A further need exists for a request to access, or otherwise utilize, the information in the bean to be automatically examined against the privacy control policy. Another need exists for the request to be denied if the privacy control policy would be violated.

SUMMARY OF THE INVENTION

In general, the present invention provides a method, system and program product for automatically managing information privacy. Specifically, when a user submits information pursuant to a web transaction, the information is stored in a bean. As indicated above, a bean is a program component that generally includes data (i.e., the information) and methods (i.e., procedures that operate on the data). Under the present invention, the bean is packaged with a privacy control policy that sets forth privacy rules governing the access and/or use of the information. Then, when a request is later made to access or otherwise utilize the information, the reason for the request will be examined against the privacy control policy. If the request does not violate any privacy control rules, the requested access will be granted. This automatic management of information privacy can be used alone or in conjunction with access control. In the case of the latter, information corresponding to the requestor would be examined against an access control policy that is also packaged with the bean. This will ensure that the requestor is authorized to access the information in the first place.

According to a first aspect of the present invention, a method for automatically managing information privacy is provided. The method comprises: receiving a request that includes a call for information in a bean, which stores information and methods for operating on the information, and a purpose for the call, the purpose indicating a manner in which a requestor of the information intends to use the information; and automatically determining whether the request should be granted by comparing the purpose to a privacy control policy, which sets forth privacy rules governing circumstances under which the information particular to the bean can be accessed and used, that is packaged with the bean to determine whether the purpose is valid, the privacy control policy being additional to the information and the methods and being packaged as an elements of a deployment descriptor.

According to a second aspect of the present invention, a computer-implemented method for automatically managing information privacy is provided. The method comprises: receiving a request that includes a call for information in a bean and a purpose for the call, the purpose indicating a manner in which a requestor of the information intends to use the information, wherein the call is to a method within the bean, and wherein the method references at least one privacy control rule, which governs at least one of access or use of the information, that is packaged with the bean, the privacy control rule being additional to the information and methods of the bean and being packaged as an element of a deployment descriptor; and automatically determining whether the request should be granted by comparing the purpose to the at least one privacy control rule to determine whether the purpose is valid, wherein the request is granted if the purpose complies with the at least one privacy control rule.

Therefore, the present invention provides a method, system and program product for automatically managing information privacy.

BRIEF DESCRIPTION OF THE DRAWINGS

These and other features of this invention will be more readily understood from the following detailed description of the various aspects of the invention taken in conjunction with the accompanying drawings in which.

Figure 1:
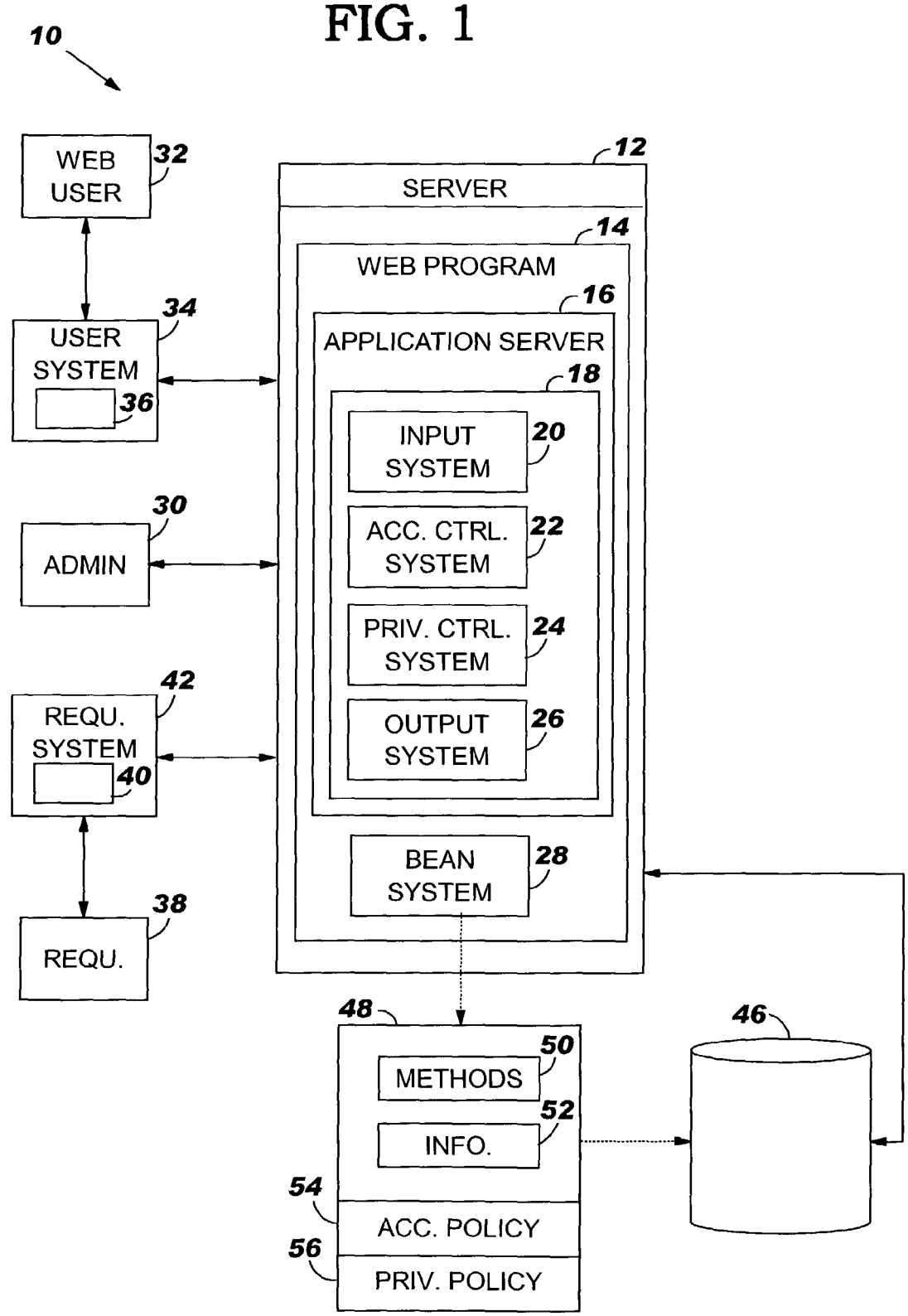
FIG. 1 depicts a system for automatically managing information privacy, according to the present invention.

The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

In general, the present invention provides a method, system and program product for automatically managing information privacy. Specifically, when a user submits information pursuant to a web transaction, the information is stored in a bean. As mentioned above, a bean is a program component that generally includes data (i.e., the information) and methods (i.e., procedures that operate on the data). Under the present invention, the bean is packaged with a privacy control policy that sets forth privacy rules governing the access and/or use of the information. Then, when a request is later made to access or otherwise utilize the information, the reason for the request will be examined against the privacy control policy. If the request does not violate any privacy control rules, the requested access will be granted. This automatic management of information privacy can be used alone or in conjunction with access control. In the case of the latter, information corresponding to the requestor would be examined against an access control policy that is also packaged with the bean. This will ensure that the requestor is authorized to access the information in the first place.

Referring now to FIG. 1 a system 10 for controlling information privacy (and access) according to the present invention is shown. As depicted, server 12 includes web program 14 that itself includes application server 16 and bean system 28. In general, web program 14 is any program that facilitates the creation and management of world wide websites. One example of such a program is WEBSPHERE, which is commercially available from International Business Machines Corp. of Armonk, N.Y. Application server 16 can be any server program on a computer in a distributed network that provides the business logic for an application program. One example of an application server is WEBSPHERE APPLICATION SERVER which is part of the WEBSPHERE program referenced above.

In a typical embodiment, the beans used hereunder are JAVABEANS and, more particularly, ENTERPRISE JAVABEANS. However, it should be understood that the teachings described herein could be implemented with any bean or bean-like structure that is capable of storing information and procedures for operating on the information.

Also shown within web program 14 is bean system 28. Bean system 28 will be described in more detail below, but is generally intended to represent any system that allows for the creation and deployment of beans as well as for the storage of information therein. As explained above, a bean is a program component that includes information and methods. The methods are procedures that perform some operation on the information. For example, upon being called, a method can use a stored e-mail address to send a confirmation e-mail. Under the present invention, administrator 30 can interface with bean system 28 to create a bean "template" from which future beans will be created. Any bean(s) 48 created based on the bean "template" will store information 52 as well as any desired method(s) 50 for operating on information 52. The bean 48 will also be packaged with privacy control policy 56 and, optionally, access control policy 54. These policies are typically packaged with bean 48 as a "deployment descriptor." An access control policy 54 is a set of rules that dictates who can access the information. Typically, the access control rules could set forth user names and passwords of particular individuals that are permitted to access information 52. A privacy control policy 56 is a set of privacy rules that dictates the circumstances in which information 52 can be accessed and/or used. For example, a privacy control rule could state that "an e-mail address can only be accessed to generate and send a confirmation e-mail." In any event, once policies 54 and 56 are identified, the methods 50 in the beans would contain specific references thereto. Thus, for example, if a call to a method 50 for sending an e-mail message was received, the method 50 could first refer to one or more rules within access control policy 54 to verify that the call was received from an individual who had permission to access the necessary information (e.g., the intended recipient's e-mail address). If the individual is authorized, one or more rules in privacy control policy 56 would be referenced to ensure that the information was being used for a compliant purpose.

In any event, once administrator 30 has created a bean "template" (i.e., and packaged the same with any applicable policies), the bean "template" can be deployed. Then, when web user 32 conducts a commercial transaction, any information web user 32 provides will be stored in a particular instance of the bean template, namely, bean 48. The process by which web user 32 conducts a web transaction is generally well known. Specifically, web user 32 will manipulate user interface 36 (e.g., a web browser) within user system 34 (e.g., a personal computer) to transmit a web request to server 12. As indicated above, the web request could be for any purpose such as for ordering a product online. Any information supplied by web user 32 when sending the web request (e.g., credit card numbers, e-mail address, etc.) will be received by server 12. Upon receipt, bean system 28 will generate bean 48 as a new instance of the bean "template" created by administrator 30 and store web user 32's information therein. Accordingly, information for each web user/transaction will be stored in its own bean. This is so that information for web user "A" is stored in bean "A," while information for web user "B" is stored in bean "B." Once web user 32's information 52 has been stored, the bean 48 could be stored in database 46.

Under the present invention, when information is stored in bean 48 in this manner, access control and privacy control can be automatically ensured. Specifically, if requestor 38 attempts to access and/or use information stored in a bean 48, the present invention will automatically verify whether such access and/or use is permissible. As shown, requestor 38 can issue a request using requesting program 40 within requesting system 42. Requesting system 42 can represent any computerized system that communicates with server 12. For example, requesting system 42 could be a workstation operated by an employee of the company with which web user 32 placed the web request containing his/her information. Requesting program 40 could be any application software that is used by requestor 38, and which requests access to or use of information in a bean. For example, requesting program 40 could be a program that uses information to generate and send marketing e-mail messages. In this case, requestor 38 could be an individual or group of individuals in a marketing department that is seeking to send marketing e-mail messages to existing customers. To obtain an e-mail address, requesting program 40 will generate and transmit a request to server 12. The request will generally include a call to one or more applicable methods within a bean (based on what piece (s) of information is needed), a purpose for the call, as well as user information corresponding to requestor 38. In a typical embodiment, the request is generated automatically by requesting program 40 to help minimize potential tampering with by requestor 38. For example, if requesting program 40 is a program for transmitting marketing media electronically, the reason stated in the request would be similar to: "for transmitting marketing media electronically." This would prevent requester 38 from using a false information and/or purpose for obtaining information.

When the request is received by server 12, control system 18 will facilitate the automatic access and privacy controls of the present invention. As shown, control system 18 includes input system 20, access control system 22, privacy control system 24 and output system 26. A request sent from requesting system 42 will be received by input system 20, which will retrieve the appropriate bean. For example, if the request is to obtain web user "A's" information, input system 20 would retrieve bean "A" from database 46. Once the appropriate bean 48 has been accessed, the call in the request will be invoked will invoke the appropriate method(s) 50 in bean 48. As indicated above, the method(s) 50 not only perform some operation on information 52 (e.g., retrieval, utilization, etc.), but also include references to access control rules (optional) and privacy control rules. If the called method(s) 50 reference access control rules within access control policy 54, access control will be automatically performed first. In a typical embodiment, the referenced access control rules will set forth the user names and passwords for all authorized (or known unauthorized) requesters. Once these user names and passwords are known, the user name and password supplied by requester 38 in the request will be automatically compared thereto by access control system 22. If requester 38's user name and password match a valid user name and password in the referenced access control rules, access is approved. If, however, requester 38's information cannot be verified, access is denied and an error message or the like can be forwarded back to requestor 38 via output system 26.

Once access has been verified (if at all), the present invention will automatically perform privacy control in a similar manner. Specifically, the purpose stated within the request will be compared by privacy control system 24 to the set of rules referenced by method(s) 50. For example, one of the rules referenced by the called method(s) 50 could state "e-mail addresses can only be used to send confirmation e-mail messages." If, however, requesting program 40 is a program for sending marketing media, the request generated thereby would state as much in the purpose. Thus, when compared privacy control system 24, the lack of compliance with the policy would be indicated, and the request would be denied. If, however, the stated purpose in the request was to send a confirmation e-mail message, a complaint purpose would exist and the e-mail address would be returned to requestor 38 via output system 26. Alternatively, depending on the sophistication of method(s) 50, the e-mail message could be generated and sent directly by method(s) 50.

As can be seen, method(s) 50 can provide numerous functions. Specifically, they not only allow for operation (e.g., retrieval and/or use) of information 52, but also help facilitate privacy control and access control by referencing specific rules for control system 18 to utilize.

It should be understood that control system 18 has been depicted as shown for illustrative purposes only and that many variations exist. For example, input system 20 and output system 26 could exist as one combined system. In addition, where bean 28 is an ENTERPRISE JAVABEAN, application server 18 can be referred to as the "EJB runtime server." Still yet, although shown outside of application server 16, bean system 28 can actually reside anywhere within web program 14.

Figure 2:
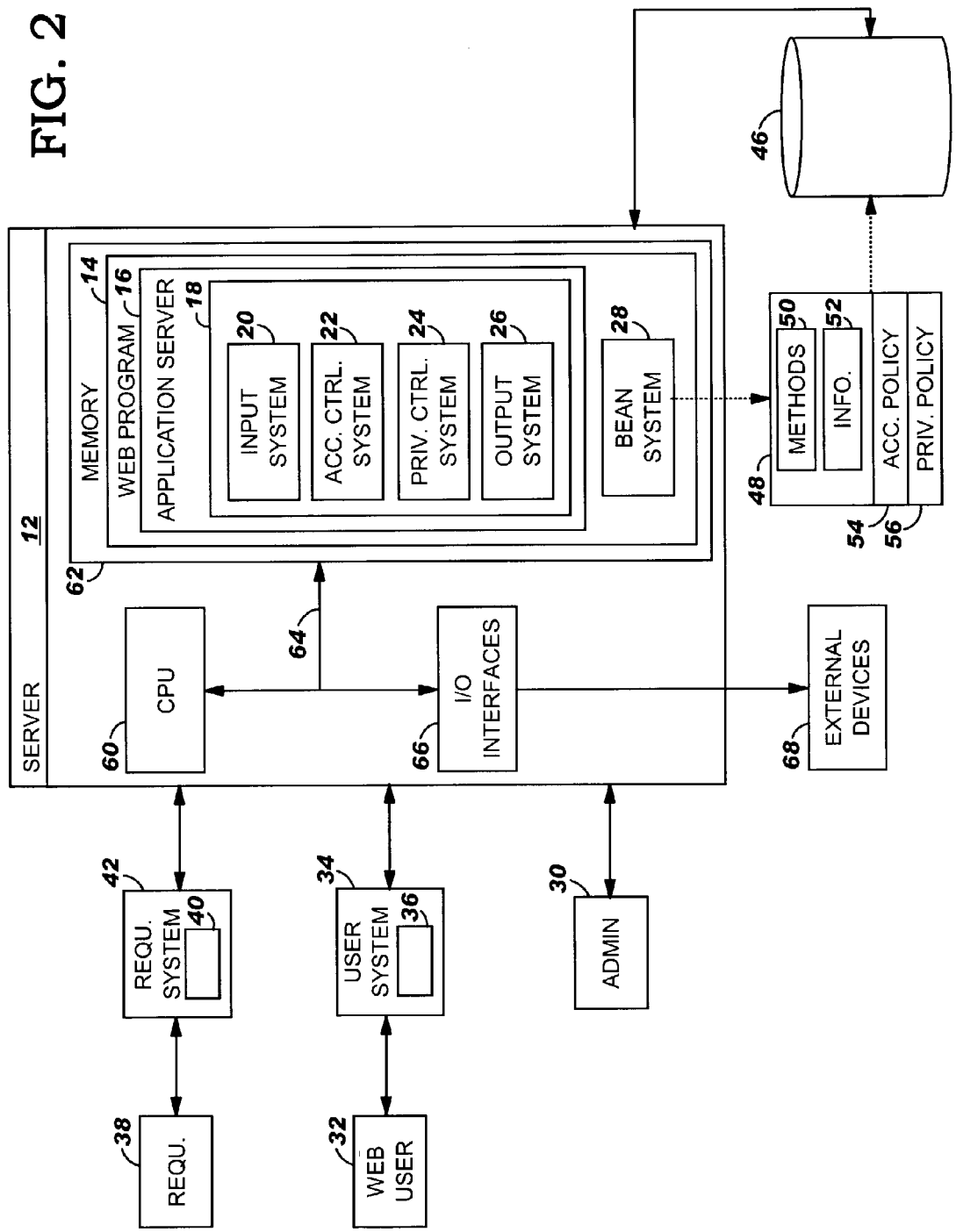
FIG. 2 depicts a more detailed depiction of system of FIG. 1

Referring now to FIG. 2, a more detailed diagram of server 12 is shown. As depicted, server 12 generally includes central processing unit (CPU) 60, memory 62, bus 64, input/output (I/O) interfaces 66 and external devices/resources 68. CPU 60 may comprise a single processing unit, or be distributed across one or more processing units in one or more locations, e.g., on a client and server. Memory 62 may comprise any known type of data storage and/or transmission media, including magnetic media, optical media, random access memory (RAM), read-only memory (ROM), a data cache, a data object, etc. Moreover, similar to CPU 60, memory 62 may reside at a single physical location, comprising one or more types of data storage, or be distributed across a plurality of physical systems in various forms.

I/O interfaces 66 may comprise any system for exchanging information to/from an external source. External devices/resources 68 may comprise any known type of external device, including speakers, a CRT, LED screen, hand-held device, keyboard, mouse, voice recognition system, speech output system, printer, monitor, facsimile, pager, etc. Bus 64 provides a communication link between each of the components in server 12 and likewise may comprise any known-type of transmission link, including electrical, optical, wireless, etc. In addition, although not shown, additional components, such as cache memory, communication systems, system software, etc., may be incorporated into server 12.

Database 46 is optional and could provide storage for information under the present invention. Such information could include, for example, bean "templates," beans 48, access control policies, privacy control policies, methods, etc. As such, database 46 may include one or more storage devices, such as a magnetic disk drive or an optical disk drive. In another embodiment, database 46 includes data distributed across, for example, a local area network (LAN), wide area network (WAN) or a storage area network (SAN) (not shown). Database 46 may also be configured in such a way that one of ordinary skill in the art may interpret it to include one or more storage devices.

It should be understood that communication between server 12, and user system 34 and requesting system 42 can occur via a direct hardwired connection (e.g., serial port), or via an addressable connection in a client-server (or server-server) environment which may utilize any combination of wireline and/or wireless transmission methods. In the case of the latter, the server and client may be connected via the Internet, a wide area network (WAN), a local area network (LAN), a virtual private network (VPN) or other private network. The server and client may utilize conventional network connectivity, such as Token Ring, Ethernet, WiFi or other conventional communications standards. Where the client communicates with the server via the Internet, connectivity could be provided by conventional TCP/IP sockets-based protocol. In this instance, the client would utilize an Internet service provider to establish connectivity to the server. It should also be understood that although not shown for brevity purposes, user system 34 and requesting system 42 can include computerized components (e.g., CPU, memory, database, etc.) similar to server 12.

Stored in memory 62 of server 12 is web program 14. As indicated above, web program includes application server 16 and bean system 28. Application server 16 typically includes control system 18 that itself includes input system 20, access control system 22, privacy control system 24 and output system 26. Once administrator 30 has finished utilizing bean system 28 to establish a bean "template," specific instances of the template (e.g., bean 48) will be created upon submission of information from web user 32. Specifically, when web user 32 submits a web request, bean system 28 will create an instance of the bean "template" and store web user 32's information therein. As indicated above, bean 48 will include method(s) 50 and user 32's information 52, and will be packaged with a deployment descriptor that includes (optional) access control policy 54 and privacy control policy 56.

When requestor 38 issues a request (i.e., via requesting program 40 within requesting system 42), the request will be received by input system 20. The request will typically include: (1) at least one call to method(s) 50; (2) a purpose for the call; and (3) optional requestor 38 information (e.g., user name, password, etc.). Once the request has been received, input system 20 will identify the appropriate bean 48 and the call will be used to invoke method(s) 50. If access control policy 54 was provided, the user name and password will be verified. Specifically, if method(s) 50 contains a reference to one or more access control rules in a provided access control policy 54, access control system 22 will compare requestor 38's information to that in the referenced access control rules. If requestor 38 has authorization to access the requested information, access will be granted. However, if requester 38 is not authorized, access will be denied.

After access control has been automatically performed (if at all), privacy control will be automatically performed. Specifically, when called, method(s) 50 will reference at least one privacy control rule in privacy control policy 56. Such rules set forth the conditions and situations in which web user 32's information can be used. Privacy control system 24 will compare the purpose set forth in the request to the referenced privacy control rules. If the reason is compliant (i.e., valid under the rules), the request access and/or use of the information will be permitted. If, however, the reason is not compliant, access and/or use will not be granted. For example, if the referenced privacy control rules state "allow e-mail address to be used only for confirmation messages," a stated purpose of "for sending marketing media electronically" would be deemed non-compliant.

It should be understood that the use of textual rules and purposes under the present invention is for illustrative reasons only and many variations could be implemented. For example, the privacy control rules and the purposes in the requests could be numeric (or alphanumeric) codes. In this case, the privacy control rules could list only those codes that are compliant. For example, the act of sending a confirmation e-mail message could be assigned code "100" and the act of sending marketing media electronically could be assigned code "200." In such a case, the privacy control rules referenced by method(s) 50 could simply include "100." Thus, if a purpose had a code other than "100" (e.g., "200"), it would be non-compliant. The use of such codes makes comparison easier because it prevents slight differences in language from causing operational problems.

It is understood that the present invention can be realized in hardware, software, or a combination of hardware and software. Any kind of computer/server system(s)—or other apparatus adapted for carrying out the methods described herein—is suited. A typical combination of hardware and software could be a general purpose computer system with a computer program that, when loaded and executed, controls server 12 such it carries out the respective methods described herein. Alternatively, a specific use computer, containing specialized hardware for carrying out one or more of the functional tasks of the invention, could be utilized. The present invention can also be embedded in a computer program product, which comprises all the respective features enabling the implementation of the methods described herein, and which—when loaded in a computer system—is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

We claim:

1. A method for automatically managing information privacy, comprising:
receiving a request that includes a call for information in a bean, which stores information and methods for operating on the information, and a purpose for the call, the purpose indicating a manner in which a requestor of the information intends to use the information; and
automatically determining whether the request should be granted by comparing the purpose to a privacy control policy, which sets forth privacy rules governing circumstances under which the information particular to the bean can be accessed and used, that is packaged with the bean to determine whether the purpose is valid, the privacy control policy being additional to the information and the methods and being packaged as an element of a deployment descriptor.

2. The method of claim 1, wherein the call comprises a call to a method within the bean, wherein the method includes a procedure that operates on the information, and wherein the method references at least one rule in the privacy control policy.

3. The method of claim 2, further comprising:
providing the information pursuant to a web transaction; and
storing the information and the method in the bean, prior to the receiving step.

4. The method of claim 1, wherein the bean is an ENTERPRISE JAVABEAN that stores information regarding a single source.

5. The method of claim 1, wherein the privacy control policy is packaged with the bean as a deployment descriptor.

6. The method of claim 1, further comprising, in addition to comparing of the purpose to the access control policy, automatically performing access control to the information based on user information that identifies the requestor making the request and an access control policy packaged with the bean that dictates who can access the information.

7. The method of claim 1, wherein the step of automatically determining is carried out by an application server.

8. The method of claim 6, wherein the application server is WEBSPHERE application server.

9. A computer-implemented method for automatically managing information privacy, comprising:
receiving a request that includes a call for information in a bean and a purpose for the call, the purpose indicating a manner in which a requestor of the information intends to use the information, wherein the call is to a method within the bean, and wherein the method references at least one privacy control rule, which governs at least one of access or use of the information, that is packaged with the bean, the privacy control rule being additional to the information and methods of the bean and being packaged as an element of a deployment descriptor; and automatically determining whether the request should be granted by comparing the purpose to the at least one privacy control rule to determine whether the purpose is valid, wherein the request is granted if the purpose complies with the at least one privacy control rule.

10. The method of claim 9, wherein the bean is an ENTERPRISE JAVABEAN.

11. The method of claim 9, wherein the method comprises a procedure that operates on the information.

12. The method of claim 9, further comprising, in addition to comparing of the purpose to the access control policy, automatically performing access control to the information by comparing user information that identifies the requestor making the request to an access control policy that is also packaged with the bean that dictates who can access the information.

13. The method of claim 9, wherein the at least one privacy control rule is part of a privacy control policy that is packaged with the bean as a deployment descriptor.

14. The method of claim 9, wherein the step of automatically determining is performed by an application server.

15. The method of claim 9, further comprising:
providing the information pursuant to a web transaction; and
storing the information and the method in the bean, prior to the receiving step.

* * * * *